United States Patent [19]

Okada et al.

[11] Patent Number: 5,059,199

[45] Date of Patent: Oct. 22, 1991

[54] TREATING DEVICE FOR ENDOSCOPES

[75] Inventors: Tsutomu Okada, Inagi; Kazuhiro Inoue, Akigawa, both of Japan

[73] Assignee: Olympus Optical Co., Ltd., Tokyo, Japan

[21] Appl. No.: 504,539

[22] Filed: Apr. 4, 1990

[30] Foreign Application Priority Data

Apr. 12, 1989 [JP] Japan ................................. 1-42015
Dec. 4, 1989 [JP] Japan ................................. 1-140556
Mar. 6, 1990 [JP] Japan ............................. 2-22306[U]

[51] Int. Cl.$^5$ .................................................. A61B 17/22
[52] U.S. Cl. ................................................................ 606/127
[58] Field of Search ........................ 606/127, 128, 113

[56] References Cited

U.S. PATENT DOCUMENTS 4,865,017 9/1989 Shinozuka ................... 606/127 X

FOREIGN PATENT DOCUMENTS 61-9601 3/1986 Japan .
63-197443 8/1988 Japan .

Primary Examiner—Michael H. Thaler
Attorney, Agent, or Firm—Frishauf, Holtz, Goodman & Woodward

[57] ABSTRACT

A treating device is inserted into the body cavity of a subject through a sheath by freely moving an operation wire in a forward/backward direction. A treating unit is connected to the forward end of the operation wire and includes a plurality of elastic wires extending from the forward end to the back end, a tip cap for holding the forward ends of the elastic wires, and a holding member for holding the back ends of the elastic wires. The respective elastic wires have first to fifth bent points in a position from the forward end to the back end thereof. The first and fifth bent points are projected inwardly relative to the center of the treating unit and second to fourth bent points are projected outwardly away from the center of the treating unit. All sections or sides each defined between the adjacent corresponding bent points of elastic wires are inclined at given angles to the center axis of the treating unit when they are spread out from the distal end of the sheath.

9 Claims, 4 Drawing Sheets

TREATING DEVICE FOR ENDOSCOPES

BACKGROUND OF THE INVENTION

1. Field of the Invention

The present invention relates to a treating device for endoscopes, such as basket type forceps to be inserted into the body cavity of a human subject and adapted to grasp a foreign matter such as calculus, and a high-frequency type snare for resecting polyps which are produced in the body cavity of the human subject.

2. Description of the Related Art

Known in the art is a basket type forceps which is adapted to grasp a foreign object, such as calculus, produced in the body cavity of a subject, such as in the bile duct and the urinary bladder. Such ordinary basket forceps 1 is configured as shown in FIG. 8. In FIG. 8, a grasp type basket member 4 is mounted on the distal end of an operation wire 3 which is inserted into and withdrawn from a flexible sheath 2. The basket member 4 has a plurality of elastic wires 5 with their base end portions fixed by a holding member 6 to the distal end of the operation wire 3. The forward ends of the respective elastic wires 5 are held together by a tip cap 7. Intermediate sections 9 of the wires are each defined by two outwardly folded sections 8 such that each extends parallel to the center axis of the basket member 4.

The basket member 4 can be moved back and forth relative to the open distal end of the flexible sheath 2 by moving the operation wire 3 back and forth by means of an operation device, not shown.

When the basket type forceps 1 is used, the flexible sheath 2 of the basket type forceps 1 is inserted through the channel of the endoscope to allow the basket member to extend via the distal end of the endoscope. At this time, when the basket member 4 is projected from the distal end of the sheath 2 into the body cavity of the subject, it is spread open by an elastic force of each elastic wire 5 by itself and the foreign matter can be trapped there by the basket member in the spread-open state. The foreign matter can be grasped by withdrawing the basket member 4 back into the distal end portion of the flexible sheath 2.

As seen from FIG. 8, the respective elastic wires 5 of the basket member 4 of the ordinary basket forceps 1 are less in the number of bent sections 8 and the intermediate sections 9 of the basket member 4 extend in a direction parallel to that in which the operation wire 3 is moved back and forth. For this reason, the basket member is liable to be collapsed into an irregular shape. In the narrow duct or tract of the patient's body, in particular, the basket member 4 is adequately not spread open, failing to grasp a foreign matter, such as the calculus.

The basket type forceps a set forth above is disclosed, for example, in the Published Examined Japanese Utility Model Application 61-9601 and Published Unexamined Japanese Patent Application 63-197443.

SUMMARY OF THE INVENTION

It is accordingly the object of the present invention to provide a treating device for endoscopes which, when a treating unit is projected out of the distal end of a sheath, enables elastic wires of the treating unit to positively and adequately be spread out even if a body cavity of a patient is a shorter-depth duct or tract or a narrow duct or tract.

A treating device adapted to be inserted into a body cavity of a subject through a channel tube of an endoscope is provided, comprising:

(1) a sheath whose distal end is inserted through the channel tube into the body cavity;

(2) an operation wire having a forward end and a base end and inserted into the sheath through the channel tube such that it can be moved in a forward/backward direction;

(3) operation means connected to the base end of the operation wire to move it in a forward/backward direction; and (4) a treating unit connected to the forward end of the operation wire and adapted to be projected out of the sheath when the operation wire is moved in the forward direction and retracted back into the sheath when the operation wire is moved in the backward direction, the treating unit having:

(a) a plurality of elastic wires each having a forward end and a base end and each having first to fifth bent points in a position between the forward end and the base end thereof, first to fourth sections or sides each defined between the adjacent corresponding bent points, and a fifth section or side extending from the fifth bent point toward the base end thereof, where, in a free state in which the respective elastic wires are spread out, the first and fifth bent points are inwardly projected relative to the center of the treating unit, the second to fourth bent points are outwardly projected away from the center of the treating unit, and the first to fourth sections or sides are inclined at given angles to the center axis of the treating unit, (b) means for holding the respective forward ends of the elastic wires; and (c) means for connecting the respective base ends of the elastic wires, as a bundled unit, to the forward end of the operation wire.

In the treating device according to the present invention, when a treating unit is projected from the distal end of the sheath, the elastic wires defined by the outwardly projected second to fourth bent points can adequately and positively spread out, by the inwardly projected first and fifth bent points.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

The embodiments of the present invention will be explained below with reference to the accompanying drawings.

Figure 1:
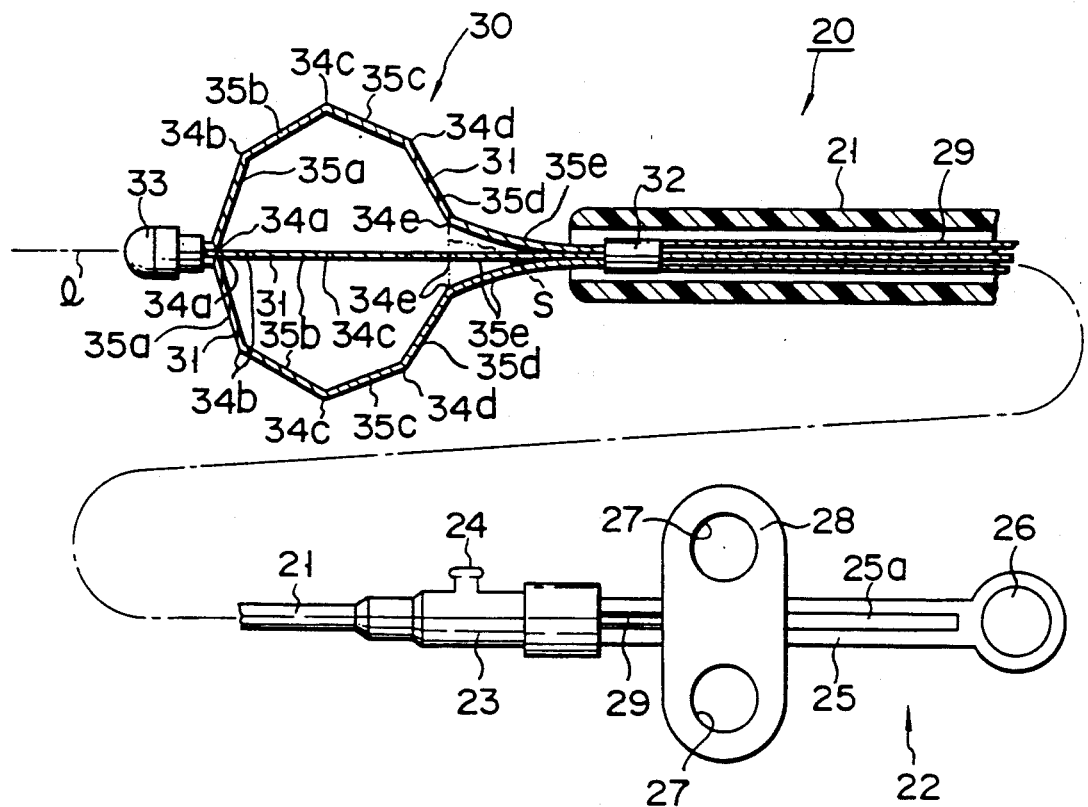
FIG. 1 is a side view showing basket type forceps, for endoscopes, according to a first embodiment of the present invention with part of a sheath shown cut away partway in cross-section.

FIG. 1 shows basket forceps for endoscopes which is embodied as a first embodiment of the present invention. The basket type forceps 20 has a flexible sheath 21 with an operation section 22 provided on the back or proximal end of the sheath. The operation of the operation section 22 will be explained below in more detail. A handling section 23 is connected to the proximal end of the sheath 21. A liquid supply inlet 24 is provided at the handling section 23 and leads to the interior of the sheath 21. A slide guide bar 25 is provided on the handling section 23 such that it extends in a backward direction. A first finger engaging section 26 is provided, as a rear end, on the slide guide bar 25. A slider 28 having a pair of second finger engaging sections 27 is provided on the guide bar 25 such that it can slide in the axial direction of the guide bar 25. The proximal end of the operation wire 29 is connected to the slider 28 to allow it to be moved back and forth.

The operation wire 29 can be moved back and forth through the sheath 21 by moving the slider 28 in the forward/backward direction. A guide groove 25a is provided in the bar 25 to allow the operation wire 29 to pass through.

A basket unit or member 30 is provided, as a treating member, on the forward end of the operation wire 29. A plurality of elastic wires 31 are provided as elastic wire sections of the basket 30. The back end portions of the respective elastic wires 31, as well as the forward end or tip portions of the operation wires 29, are held together by a holding member 32. By so doing, the basket member 30 is coupled to the forward end of the operation wire 29. The forward end portions of the respective elastic wires 31 are held together by a tip cap 33. In this way, the plurality of elastic wires 31 are held together at the forward and base ends to provide the basket member 30. In this embodiment, the elastic wires 31 of the basket member 30 are composed of four elastic wires, upper and lower and left and right. The back or base end portions of the four elastic wires 31 extend toward the proximal end and are bundled to provide the aforementioned operation wire 29.

First to fifth bent points 34a to 34e are provided in that order from the base end of the tip cap 33 toward the base end of the holding member 32 at predetermined intervals as set forth below. In a free state, the respective elastic wires 31 are externally spread into a basket-like area.

The first and fifth sections are projected toward the center axis 1 of the basket member 30 and the second to fourth sections 35b to 35d are projected away from the center axis 1 of the basket member 30 to provide a basket-like area as shown in FIG. 1.

The first to fourth sections 35a to 35d defined by the bent points 34a to 34e are provided as straight sections. The first to fourth sections 35a to 35d are inclined with respect to the center axis 1 of the basket member 30, that is, extend in a direction not parallel to the center axis 1 of the basket member 30. The angle at which the first section 35a makes is substantially equal to that at which the fourth section 35d makes. The same thing can be said of the second and third sections 35b and 35c. The inclination angles of the first and fourth sections 35a and 35d are greater than those of the second and third sections 35b and 35c. It is to be noted that the sections 35a to 35d, being straight as shown in FIG. 1, may be formed as curved sections. In this case, the inclination angles are regarded as corresponding to those angles each defined by two adjacent straight lines drawn between a shared bent point and each remote bent point of the two adjacent curve sections.

The section 35e defined between the fifth bent point 34e and the holding member 32 is slightly inclined, or gently curved, toward the center axis 1 of the basket member 30. The second to fourth straight sections 35b to 35d are substantially equal in length except for a somewhat longer section 35a and form the sides of a substantially regular polygon when the basket member 30 is spread open, that is, when in a natural state a pair of opposite elastic wires 31 or another pair of opposite elastic wires 31 are spread open in the same plane. In this embodiment, the sections (sides) 35a to 35d define a substantially regular octagon by the pair of opposite sides in plan view in that free state and, together with a section (side) S (FIG. 1) drawn between the opposite bent points 34e, define a substantially regular nonagon.

The way of grasping a foreign matter in the body cavity, such as a bilestone, and collecting it with the use of a basket member-equipped treating device for endoscopes will be explained below in more detail.

The operation wire 29 is initially withdrawn, by the operation of the operation section, back into the sheath 21 and, in this state, the distal end of the sheath 21 is projected into the body cavity of the subject via the insertion channel of an endoscope, not shown, which has initially been introduced into the body cavity of a subject. That is, the distal end of the sheath 21, which has been projected from the distal end of the insertion channel, is guided from the duodinal papilla into the common bile duct.

With the slider 28 of the operation section 22 advanced along the bar 25, the basket member 30 is projected from the distal end of the sheath 2 at which time the basket member 30 is naturally spread open, like a basket, under its own resiliency because it is initially so designed. For this reason, the calculus in the file duct can be trapped into the basket area through the wire-to-wire opening of the spread-open basket.

When the operator withdraws the operation wire 29 by pulling the slider 28 toward him or her, the basket member 30 is drawn back into the distal end portion of the sheath 21 s that the spread-open basket is compactly shrunk back into the sheath. The calculus is withdrawn either through the treating device or together with the endoscope, in the trapped state so that it is collected outside the body of the subject.

In this case, the sections (sides) 35a to 35d of the respective elastic wires 31 as defined by the first to fifth bent points 34a to 34e are inclined at given angles to the direction in which the basket member 30 is moved back and forth. Therefore, the basket member is less likely to be collapsed in a spread-open state. Since the fifth bent point 34e is projected toward the interior of the basket area, the length of the greatly spread basket member 30 is shortened to that extent and hence the basket member can readily be brought to a region of interest of the body cavity of the subject even if a duct or tract is shorter in length. A pick-up zone defined by the plurality of elastic wires 31 will not become smaller in size even if the wires are somewhat withdrawn into the sheath 21. As appreciated from the above, at the location of the bending section 35 between the bent point 34e and the holding member 32, the normally defined basket zone can be further expanded to that extent, offering the added advantage of readily trapping a somewhat greater stone (calculus), etc., at the basket zone.

Figure 2:
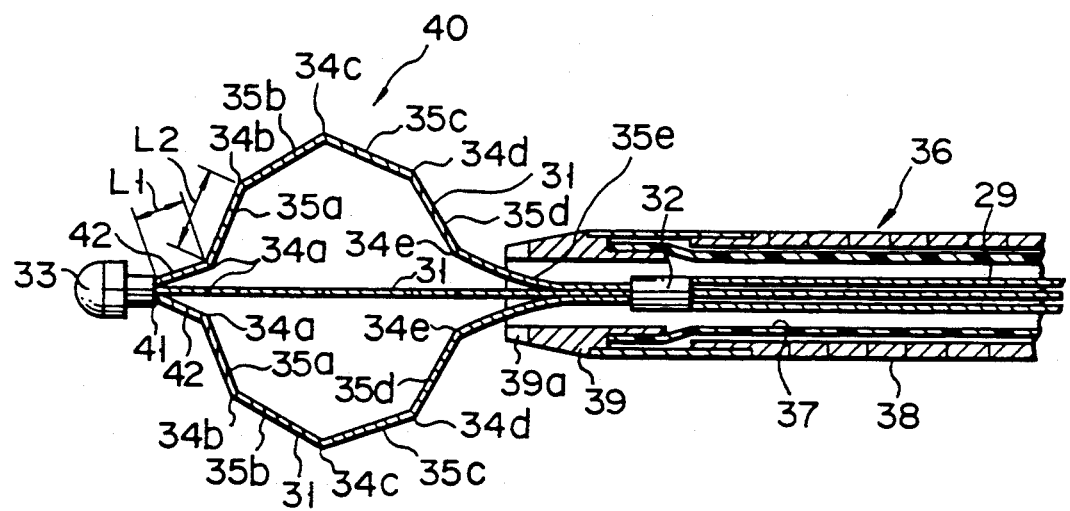
FIG. 2 is a side view showing basket type forceps, for endoscopes according to a second embodiment of the present invention with a sheath shown cut away partway in cross-section.

FIG. 2 shows basket type forceps for stone breakage which is embodied as a second embodiment of the present invention. In this embodiment, a sheath 36 is of a double wall structure having an inner tube 37 made of elastic resin and a strong outer tube 38 for buckle prevention. The outer tube 38 is formed of a closely-coiled band-like metal and a rigid tube section 39 is provided at the distal end of the sheath 36. A plurality of teeth 39a are provided for properly receiving the elastic wires 31 which are mounted on the distal end of the rigid tube section 39 as so to prevent the wires 31 from being immobably caught between a stone and the tube section 39. An operation wire 29 is inserted through the sheath 36 and a basket member 40 for stone fracture is connected to the distal end of the operation wire 29. The basket portion 40 is basically the same as that of the aforementioned first embodiment. However, the sections 42 of elastic wires 31 divergently extend from the base end of a tip cap 33 toward first bent points 34a and the bent point 34a is inwardly projected. The length $L_1$ of the section 42 from the base end of the tip cap 41 to the first bent point 34a is substantially less than the length $L_2$ of the first to fourth sections 35a to 35d.

The angle at which the first section 35a makes is equal to that the which the fourth section 35d makes. The same thing can be said of the second and third sections 35b and 35c.

After the stone in the bile duct is trapped by the basket zone of the basket type forceps, the operation wire 29 is pulled back, causing the trapped stone to be fractured by being compressed there. It is, therefore, possible to obtain the same effect as in the aforementioned first embodiment.

According to the second embodiment, since the elastic wires 31 divergently extend at the bent point 41, that is, at the base of the tip cap 33, the basket zone size can be further expanded and, further, upon projecting the basket member 40 from the sheath 36, a smaller insertion force is required at that time.

Figure 3:
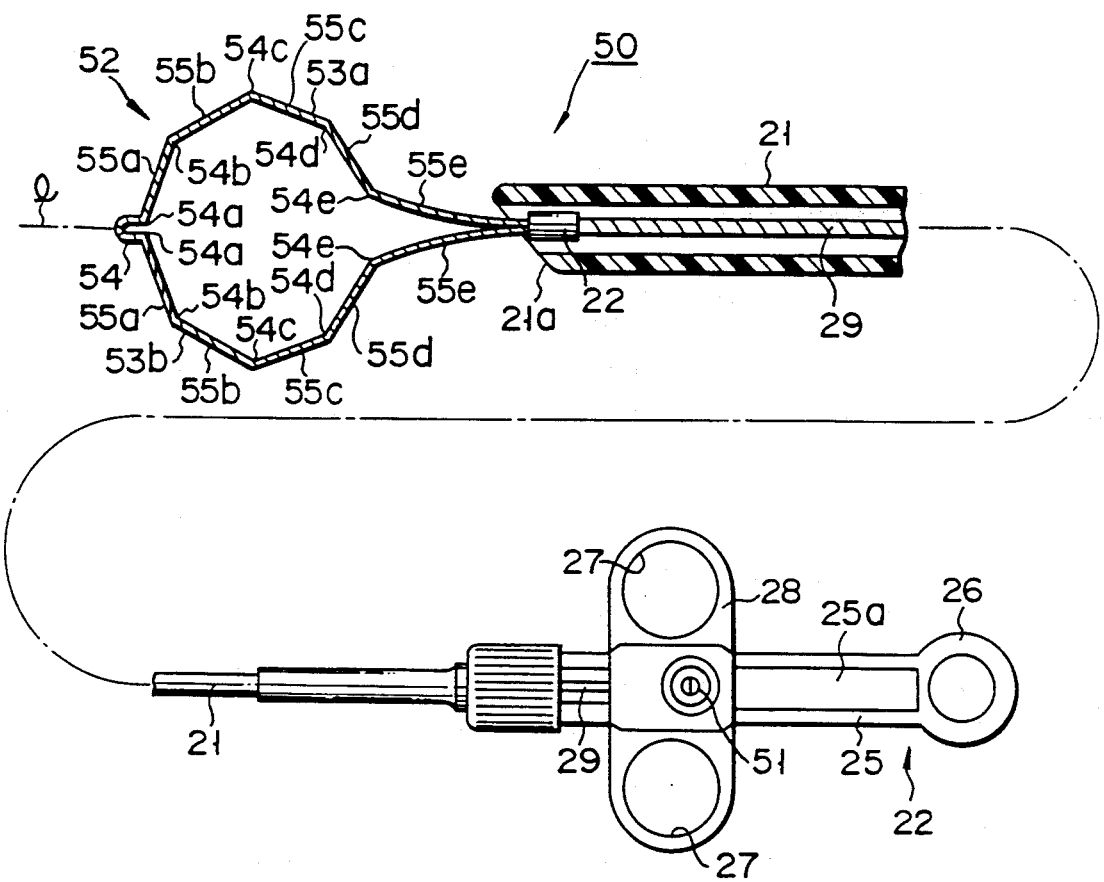
FIG. 3 is a side view showing a high-frequency snare, for endoscopes, according to a third embodiment of the present invention with part of a sheath shown cut away partway in cross-section.
Figure 8:
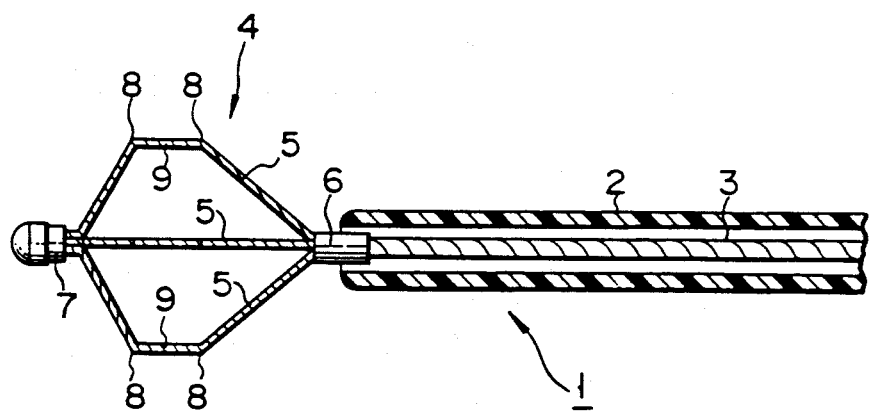
FIG. 8 is a view in longitudinal cross-section showing a distal end portion of conventional basket type forceps for endoscopes.
Figure 4:
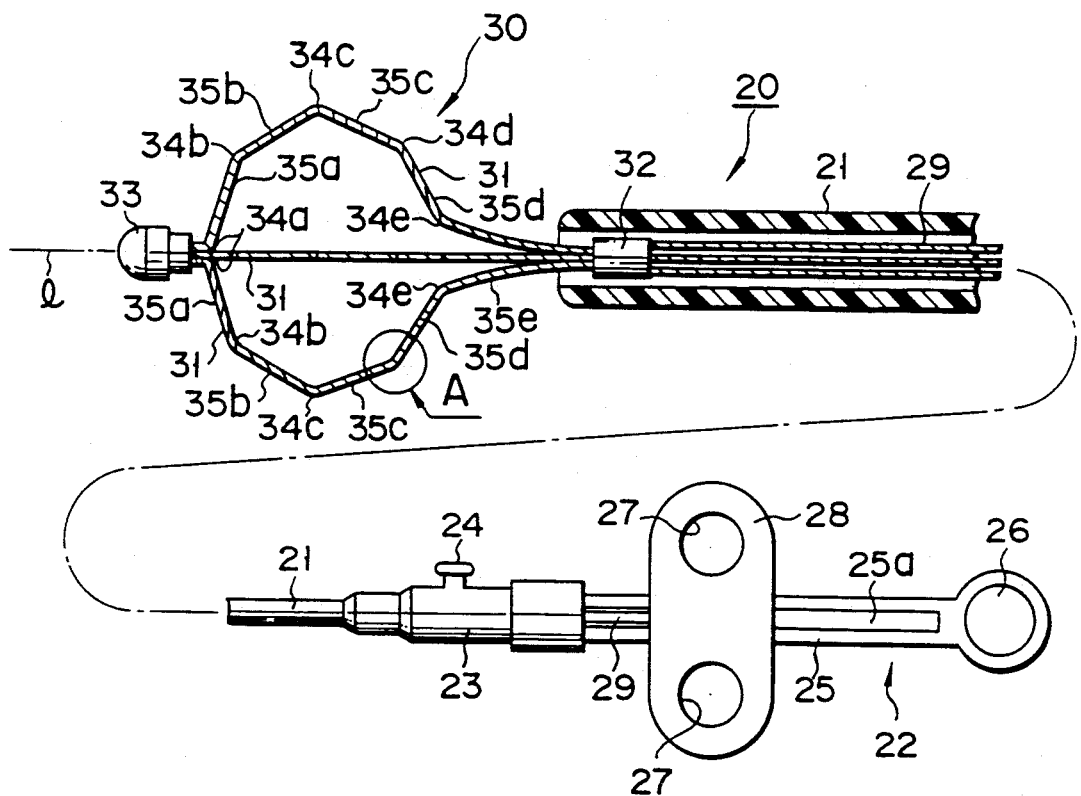
FIG. 4 is a side view showing basket type forceps according to a fourth embodiment of the present invention with its basket projected out of a sheath shown cut away partway in cross-section.

FIG. 3 shows a high-frequency snare according to a third embodiment of the present invention. The high-frequency snare 50 has a sheath 21 made of a electrically insulating material and having a forward edge 21a, as an obliquely cut edge, at the distal end to allow the ready insertion of the sheath into a channel. An operating section 22 has the same structure as in the aforementioned first embodiment.

A plug 51 is provided at a slider 28 to allow an electrical conduction to the operation wire of an electrically conductive material.

A snare loop (treating device) 52 is connected by a holding member 22 to the distal end of the operation wire 29. The snare loop 52 is formed of a single elastic wire having a bent-backed portion at which two wire segments 53a, 53b, right and left, are formed in a symmetrical relation. A pair of elastic segments 53a, 53b is connected at their end to the operating wire 29 by the holding member 22.

First to fifth bent points 54a to 54e are formed at the respective elastic segments 53a, 53b as in the aforementioned first embodiment. Sections (sides) 55a to 55d defined by the first to fifth bent points 54a to 54e are inclined at given angles all in a back/forth direction, that is, to a center axis 1 of the snare loop 52.

The sections 55e defined between the fifth bent point 54e and the holding members 22 are slightly inclined, and gently curved, relative to the center axis 1 of the snare loop 52 such that they extend from the base of the holding member toward the inside of the snare loop 52. Further, the first to fourth sections (sides) 55a to 55d are substantially equal to each other and can be spread out into a snare loop substantially corresponding to the respective sides (sections) of a regular polygon. That is, the polygon of the snare loop is the same as that of the first embodiment of the present invention.

When an affected or diseased region or tissue, such as polyp, is to be resected by the aforementioned high-frequency snare 50, the distal end of the sheath 21 is guided into the body cavity of the subject, through the channel of the endoscope, with the snare loop 52 held in the sheath 21 in a compact unit. When the operation wire 29 is moved forward under an observation by the operator with the assistance of the endoscope, the held snare is moved out of the distal end of the sheath 21 and spread out, as a snare loop 52, under its own resiliency of the elastic wire segments 53a, 53b. By doing so, a polyp is trapped by the snare loop 52 and, upon a pull back of the operation wire 29 by the operator, the snare loop 52 is retracted back into the sheath 21 to allow the neck of the polyp to be tightened thereby. A high-frequency current is conducted to the snare loop 52 by the operation wire 29, that is, by a high-frequency generator which is connected by a cord, not shown, to the plug of the operation section 22. In this way, the polyp is cauterized and removed. According to the high-frequency snare 50 thus formed, it is also possible to obtain the same advantage as that of the first embodiment.

FIGS. 4 to 7 shows basket type forceps according to a fourth embodiment of the present invention. The basket type forceps is basically the same as the basket forceps 20 of the aforementioned first embodiment of the present invention, but is different from the latter in the following respects.

Figure 5:
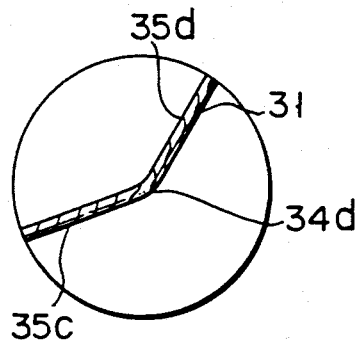
FIG. 5 is an enlarged view showing an area A in FIG. 4.

That is, first to fifth bent points 34a to 34e of elastic wires 31 of the basket member 30 are provided as outwardly and smoothly bent or curve spots, one (the fourth curved spot 34d) of which is shown, for example, in an enlarged form in FIG. 5.

Figure 6:
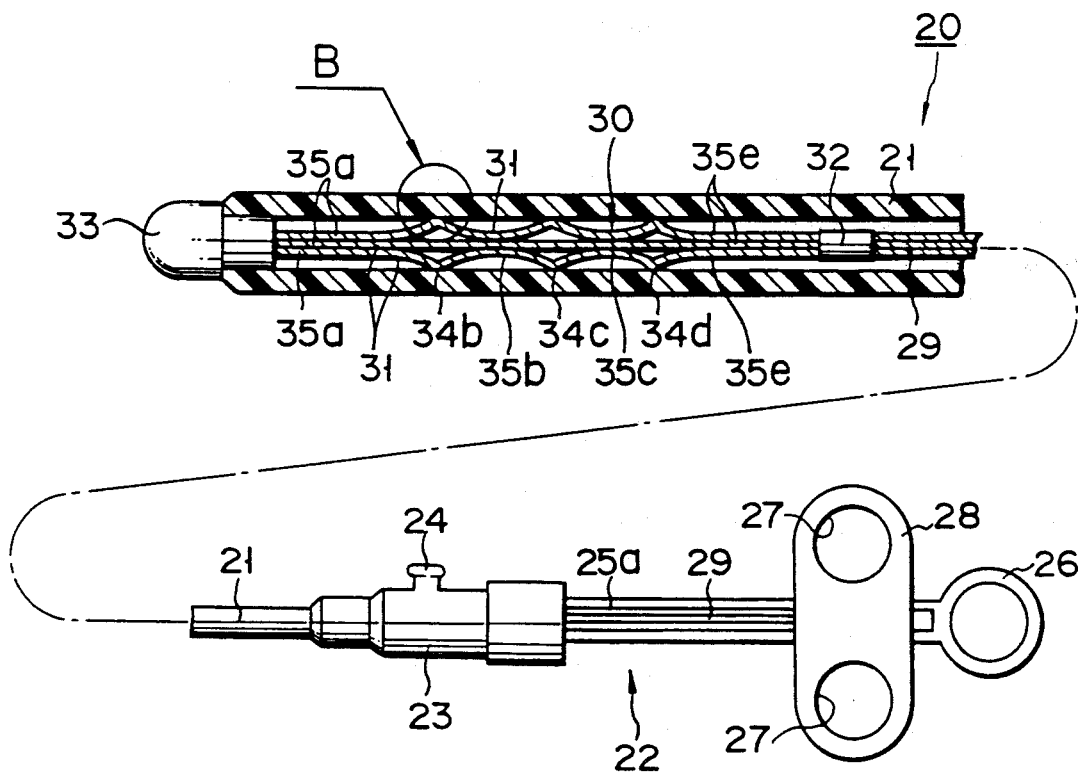
FIG. 6 is a side view showing basket type forceps according to the fourth embodiment of the present invention with a basket retracted back into a sheath which is partially shown in cross-section.
Figure 7:
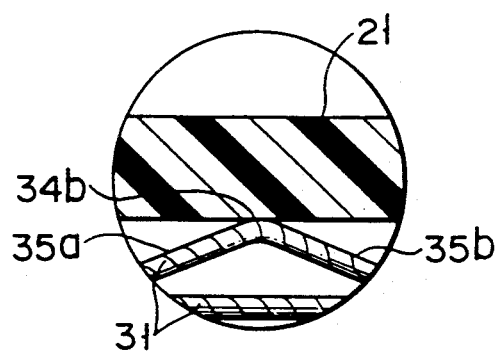
FIG. 7 is an enlarged view showing an area B in FIG. 6.

FIG. 6 shows a state in which a basket member 30 is compactly retracted back into the distal end portion of a sheath 21 with elastic wires 31 held in contact with the inner surface of the sheath. In particular, the second to fourth bent spots 34b to 34d are firmly abutted against the inner surface of the sheath 21, but do not bite in the inner wall of the sheath 21, made of resin, due to these bent spots smoothly curved. These bent spots are smoothly slidable on the inner wall of the sheath without being caught there. Thus, the basket member 30 can be retracted back into the distal end portion of the sheath 21 by a light operation. It is also possible to project the basket member out of the sheath 21 by a light operation, and hence to require a lesser amount of operation force upon the movement of the basket member into and out of the sheath and improve the operability. Since the first and fifth bent spots 34a and 34e are smoothly curved, the elastic wires 31 never bite into the inner wall of the sheath 21 even if their bent spots are abutted against the inner surface of the sheath 21.

In the aforementioned embodiment, the curved spots 34a to 34e are not pointed, that is, are smoothly formed as rounded spots. As a variant, only bent spots 34b to 34d may be provided as outwardly and smoothly curved ones in which case they can be smoothly guided into and out of the distal end portion of the sheath.

Additional advantages and modifications will readily occur to those skilled in the art. Therefore, the invention in its broader aspects is not limited to the specific details, representative devices, shown and described herein. Accordingly, various modifications may by without departing from the spirit or scope of the general inventive concept as defined by the appended claims and their equivalents.

What is claimed is:

1. A treating device adapted to be inserted into a body cavity of a subject through a channel of an endoscope, comprising:
   (1) a sheath having a forward end and a back end, said forward end being adapted to be inserted through said channel into said body cavity;
   (2) an operation wire having a forward end and a rear end, said operation wire being inserted into said sheath and adapted to be inserted through said channel such that said operation wire can be moved in both a forward and a backward direction;
   (3) operation means connected to said rear end of said operation wire to move said operation wire both in said forward and said backward direction; and
   (4) a treating unit having a center axis and connected to said forward end of said operation wire, said treating unit being projected out of said sheath when said operation wire is moved in said forward direction, and being retracted back into said sheath when said operation wire is moved in said backward direction, said treating unit having:
   (a) a front end and a back end each respectively positioned on said center axis;
   (b) a plurality of elastic wires connected between said front end and said back end, each of said plurality of elastic wires having:
   first, second, third, fourth and fifth bent points provided, in order, between said front end and said back end;
   first, second, third, and fourth sections respectively positioned, in order, between said first, second, third, fourth and fifth bent points;
   a fifth section extending from said fifth bent point toward said back end of said treating unit; and
   a sixth section extending from said first bent point toward said front end of said treating unit;
   said treating unit upon projection from said sheath having:
   said first and fifth bent points projected inwardly towards said center axis of said treating unit;
   said second, third and fourth bent points projected outwardly away from said center axis of said treating unit;
   said first, second, third and fourth sections being inclined at predetermined angles relative to said center axis of said treating unit;
   and said fifth and sixth sections being inclined at given angles relative to said center axis of said treating unit;
   said first and fifth bent points being positioned preselected distances away from said center axis;
   said first and fifth bent points moving toward and away from said center axis of said treating unit as said treating unit is moved respectively in said backward and said forward directions while substantially maintaining the shape of said treating unit;
   holding means for holding said sixth section of each of said plurality of elastic wires together at said front end of said treating unit; and
   connecting means for connecting said fifth section of each of said plurality of elastic wires as a bundled unit to said forward end of said operation wire.

2. The treating device according to claim 1, wherein said first, second, third and fourth sections of each of said plurality of elastic wires are substantially equal in length to each other.

3. A treating device according to claim 2, wherein each of said sections has a length and wherein said length of said sixth section is approximately half of said length of said first, second, third and fourth sections.

4. The treating device according to claim 1, wherein said fifth section of each of said plurality of elastic wires is internally curved toward said center axis of said treating unit.

5. The treating device according to claim 1, wherein, upon retraction of said treating unit into said sheath, at least one of said bent points of each of said plurality of elastic wires flexes to be smoothly curved as said at least one of said bent points of each of said plurality of elastic wires enters and is slidably guided in the sheath.

6. The treating unit according to claim 1, wherein at least one of said plurality of elastic wires is bent back at a mid-portion thereof, and wherein said bent back midportion is held at said front end of said treating unit by said holding means.

7. The treating unit according to claim 6, wherein each of said plurality of elastic wires has a first and a second end portion and wherein said connecting means holds said first and second end portions of each of said plurality of elastic wires in said bundled unit.

8. A treating device according to claim 1, wherein each of said plurality of elastic wires is formed of four elastic wire elements.

9. A treating device according to claim 1, wherein said fifth bent point is more distant from said center axis of said treating unit than said first bent point when said first and fifth bent points are measured in a direction perpendicular from said center axis of said treating unit.

* * * * *

UNITED STATES PATENT AND TRADEMARK OFFICE
CERTIFICATE OF CORRECTION

PATENT NO. : 5,059,199

DATED : October 22, 1991

INVENTOR(S) : OKADA et al

It is certified that error appears in the above-identified patent and that said Letters Patent is hereby corrected as shown below:

Title page, under Section [30] Foreign Application Priority Data:

Change the first and second Japanese Applications Nos.

"1-42015" to --1-42015[U]-- and

"1-140556" to --1-140556[U]--.

Signed and Sealed this

Twenty-third Day of March, 1993

Attest:

STEPHEN G. KUNIN

*Attesting Officer*  *Acting Commissioner of Patents and Trademarks*